United States Patent [19]
Brucker et al.

[11] Patent Number: 6,017,338
[45] Date of Patent: *Jan. 25, 2000

[54] FLUID COOLED AND PERFUSED TIP FOR A CATHETER

[75] Inventors: Gregory G. Brucker, Minneapolis, Minn.; Jerome Philip Saul, Newton, Mass.; Steven D. Savage, Brooklyn Center, Minn.

[73] Assignee: Angeion Corporation, Brooklyn Park, Minn.

[*] Notice: This patent is subject to a terminal disclaimer.

[21] Appl. No.: 08/496,947

[22] Filed: Jun. 30, 1995

Related U.S. Application Data

[63] Continuation-in-part of application No. 08/171,213, Dec. 21, 1993, Pat. No. 5,462,521.

[51] Int. Cl.$^7$ ............................................. A61B 17/39
[52] U.S. Cl. .................... 606/41; 606/49; 606/122; 607/99; 607/105; 607/113
[58] Field of Search .................. 606/41, 49; 607/122, 607/99, 105, 113; 128/642; 600/374

[56] References Cited

U.S. PATENT DOCUMENTS

| | | |
|---|---|---|
| 4,360,031 | 11/1982 | White . |
| 4,506,680 | 3/1985 | Stokes . |
| 4,577,642 | 3/1986 | Stokes . |
| 4,844,099 | 7/1989 | Skalsky et al. . |
| 4,917,106 | 4/1990 | Olivier . |
| 5,002,067 | 3/1991 | Berthelson et al. . |
| 5,179,962 | 1/1993 | Dutcher et al. . |
| 5,217,028 | 6/1993 | Dutcher et al. . |
| 5,242,441 | 9/1993 | Avitall . |
| 5,246,436 | 9/1993 | Rowe . |
| 5,313,943 | 5/1994 | Houser et al. . |
| 5,318,014 | 6/1994 | Carter . |
| 5,334,193 | 8/1994 | Nardella ................................. 607/99 |
| 5,423,811 | 6/1995 | Imran et al. . |
| 5,462,521 | 10/1995 | Brucker et al. ...................... 604/20 |
| 5,609,151 | 3/1997 | Mulier et al. ...................... 607/105 |

FOREIGN PATENT DOCUMENTS

| | | | |
|---|---|---|---|
| 1690786 | 11/1991 | U.S.S.R. | ................................. 606/41 |

OTHER PUBLICATIONS

Article entitled "Pacific Sintered Metals".

Dialog summary of abstracts and titles in the scientific and medical device databases, pp. 1–9.

Bergau et al, "Porous Metal Tipped Catheter . . . ", Circulation, vol. 88, No. 4, Part 2, Oct. 1993, p. I–164 (Copy 606/41).

*Primary Examiner*—Lee S. Cohen
*Attorney, Agent, or Firm*—Brad Pedersen

[57] ABSTRACT

The invention relates to an ablation catheter which controls the temperature and reduces the coagulation of biological fluids on a tip of a catheter, prevents the impedance rise of tissue in contact with the catheter tip, and maximizes the potential energy transfer to the tissue, thereby allowing an increase in the lesion size produced by the ablation. The ablation catheter includes a catheter body. The ablation catheter also includes a tip for monitoring electrical potentials, and applying electrical energy to a biological tissue. A fluid source is positioned at one end of the catheter for supplying a fluid flow through the catheter to the tip means. Passages are positioned within the tip in a variety of manners for directing the fluid flow through the tip means to the exterior surface of the tip to control the temperature and form a protective fluid layer around the tip. Monitoring structure is also positioned within the tip structure for measurement of the electrical potentials in a biological tissue. Ablation structure is also positioned within the tip for application of ablative energy to the biological tissue.

21 Claims, 3 Drawing Sheets

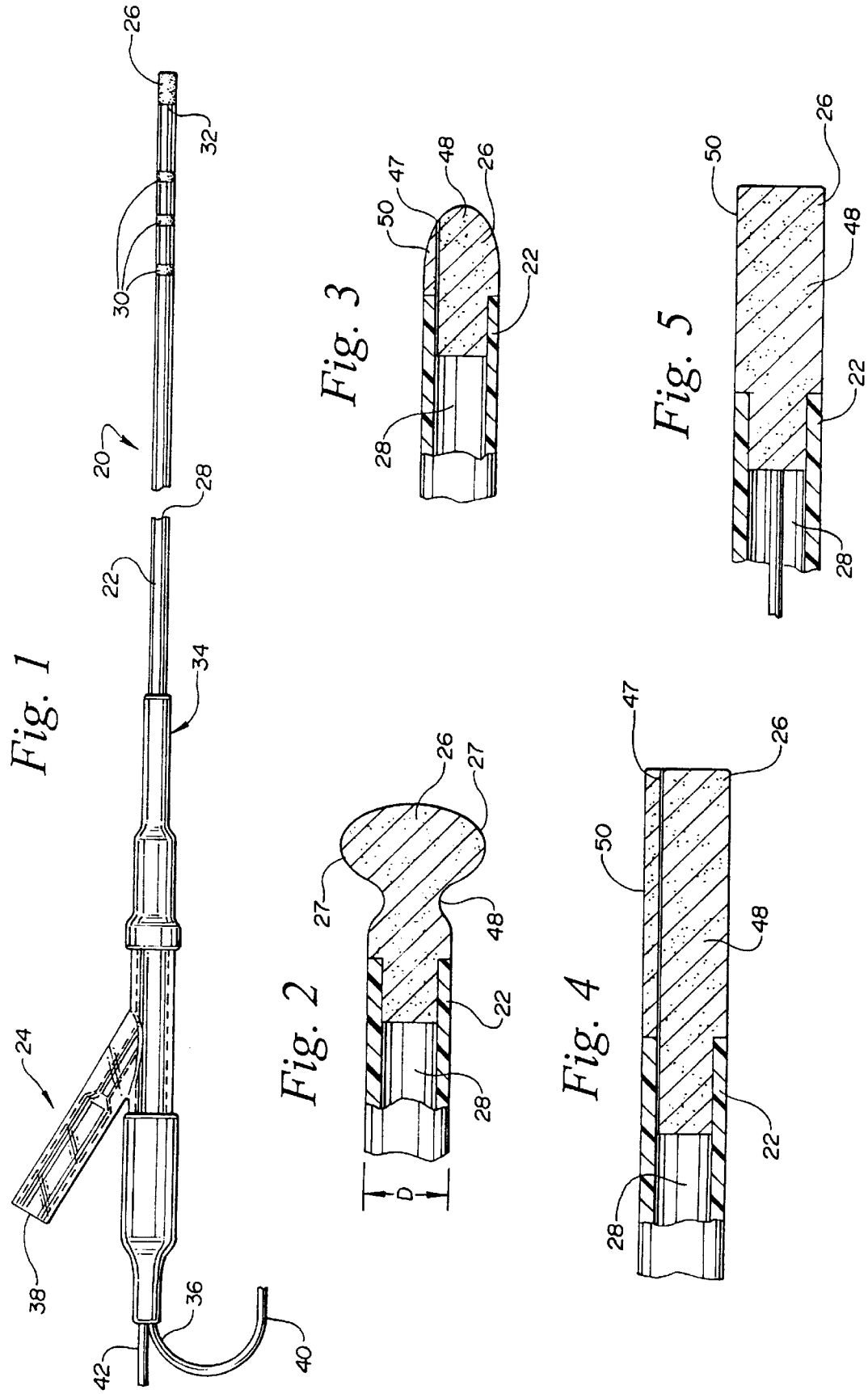

FLUID COOLED AND PERFUSED TIP FOR A CATHETER

CROSS-REFERENCE TO RELATED APPLICATION

This application is a Continuation-In-Part of U.S. application Ser. No. 08/171,213, filed Dec. 21, 1993, now U.S. Pat. No. 5,462,521, issued Oct. 31, 1995. Additionally, the subject matter of this application is related to that of U.S. application Ser. No. 08/361,329, filed Dec. 21, 1994, now U.S. Pat. No. 5,643,197, issued Jul. 1, 1997.

FIELD OF THE INVENTION

The invention relates to catheters. More specifically, the invention relates to a fluid perfused tip used on the distal end of an ablation catheter.

BACKGROUND OF THE INVENTION

The pumping action of the heart is controlled in an orderly manner by electrical stimulation of myocardial tissue. Stimulation of this tissue in the various regions of the heart is controlled by a series of conduction pathways contained within the myocardial tissue. The impulse to stimulate is started at the sino-atrial (SA) node and is transmitted through the atria. The signals arrive at the atrio-ventricular (AV) node which is at the junction of the atria and ventricles. The signal passes through the AV node into the bundle of HIS, through the Purkinje fiber system and finally activates the ventricular muscle. At the completion of ventricular stimulation, heart tissue rests to allow the cells to recover for the next stimulation. The stimulation is at the cellular level, and is a changing of the polarity of the cells from positive to negative.

Cardiac arrhythmias arise when the pattern of the heartbeat is changed by abnormal impulse initiation or conduction in the myocardial tissue. The term tachycardia is used to describe an excessively rapid heartbeat resulting from repetitive stimulation of the heart muscle. Such disturbances often arise from additional conduction pathways which are present within the heart either from a congenital developmental abnormality or an acquired abnormality which changes the structure of the cardiac tissue, such as a myocardial infarction.

One of the ways to treat such disturbances is to identify the conductive pathways and to sever part of this pathway by destroying these cells which make up a portion of the pathway. Traditionally, this has been done by either cutting the pathway surgically, freezing the tissue, thus destroying the cellular membranes, or by heating the cells, thus denaturing the cellular proteins. The resulting destruction of the cells eliminates their electrical conductivity, thus destroying, or ablating, a certain portion of the pathway. By eliminating a portion of the pathway, the pathway may no longer maintain the ability to conduct, and the tachycardia ceases.

One of the most common ways to destroy tissue by heating has been the use of electromagnetic energy. Typically, sources such as radiofrequency (RF), microwave, ultrasound, and laser energy have been used. With radiofrequency energy, a catheter with a conductive inner core and a metallic tip are placed in contact with the myocardium and a circuit is completed with a patch placed on the patient's body behind the heart. The catheter is coupled to a radiofrequency generator such that application of electrical energy creates localized heating in the tissue adjacent to the distal (emitting) electrode. Because of the nature of radiofrequency energy, both the metallic tip and the tissue are heated simultaneously. The peak tissue temperatures during catheter delivered application of RF energy to myocardium occur close to the endocardial surface, such that the lesion size produced is approximately limited by the thermodynamics of radial heat spread from the tip. The amount of heating which occurs is dependent on the area of contact between the electrode and the tissue and the impedance between the electrode and the tissue. The higher the impedance, the lower the amount of energy transferred into the tissue.

One of the major problems with radiofrequency energy is the coagulation of blood onto the tip of the catheter, creating a higher impedance or resistance to passage of electrical energy into the tissue. As the impedance increases, more energy is passed through the portion of the tip without coagulation, creating even higher local temperatures and further increasing coagulum formation and the impedance. Finally enough blood is coagulated onto the tip such that no energy passes into the tissue. The catheter must now be removed from the vascular system, the tip area cleaned and the catheter repositioned within the heart at the desired location. Not only can this process be time consuming, but it may be difficult to return to the previous location because of the reduced electrical activity in the regions which have been previously ablated. Use of temperature sensors in the tip to modulate the power input to keep the electrode below the coagulation temperature of blood have been used. These systems inherently limit the amount of power which can be applied. Others have used closed loop cooling systems to introduce water into the tip, but these systems are larger than necessary because the coolant must be removed from the catheter.

Increase of impedance was noted in radiofrequency (RF) ablation at power levels above 7 watts (W) due to the formation of a thin insulating layer of blood degradation products on the electrode surface. Wittkampf, F. H. et al., *Radiofrequency Ablation with a Cooled Porous Electrode Catheter,* Abstract, JACC, Vol. 11, No. 2, Page 17A (1988). Wittkampf utilized an open lumen system at the distal electrode which had several holes perpendicular to the central lumen which could be cooled by saline. Use of the saline kept the temperature of the electrode at a temperature low enough so that the blood products would not coagulate onto the tip of the electrode.

Impedance rise associated with coagulum formation during RF catheter ablation was also noticed by Huang et al., Increase in the Lesion Size and Decrease in the Impedance Rise With a Saline Infusion Electrode *Catheter for Radiofrequency Catheter Ablation,* Abstract, *Circulation,* Vol. 80, No. 4, page II-324 (1989). A quadropolar saline infusion intraluminal electrode catheter was used to deliver RF energy at different levels.

SUMMARY OF THE INVENTION

The invention relates to a catheter tip for cardiac signal measurement and monitoring, including a tip structure which is positioned at the end of the catheter. Path means are formed within the tip structure for directing a fluid from the interior of the tip structure to portions of the tip structure exterior surface, thereby providing a fluid protective layer surrounding the tip structure. Monitoring means are also included within the catheter tip structure for measurement of electrical potentials in a biological tissue.

The invention also relates to a catheter tip for use in cardiac signal measurement which includes a tip structure comprising a ceramic insulating material. Path means are formed within the tip structure for directing the flow of the fluid through the tip structure to provide a fluid protective layer surrounding the tip structure. Monitoring means are also included within the tip structure for measurement of electrical potentials in biological tissue.

The invention also relates to an ablation catheter which reduces the coagulation of biological fluids on a tip of a catheter, regulates the impedance rise of tissue in contact with the catheter tip, and maximizes the potential energy transfer to the tissue, producing a larger size lesion. The ablation catheter includes a catheter body. The ablation catheter also includes a tip for monitoring electrical potentials, and applying electrical energy to a biological tissue. A fluid source is positioned at one end of the catheter for supplying a fluid flow through the catheter to the tip means. Passages are formed within the tip for directing the fluid flow through the tip means to the exterior surface of the tip means to form a protective fluid layer around the tip. Monitoring means are also positioned within the tip structure for measurement of the electrical potentials in a biological tissue. Ablation means are also positioned within the tip means for application of ablative energy to the biological tissue.

The invention also relates to a method of reducing coagulation of biological fluids on a catheter tip, minimizing the resistance to energy transfer to tissue, and maximizing the potential energy transfer to the tissue in communication with the catheter tip, thereby producing an increased lesion size in the tissue. A catheter with a tip having passages is positioned within the body. A fluid flow is directed through the catheter. The fluid flow is passed through the passages in the catheter tip in a radial direction. A fluid layer is formed around the catheter tip to maintain biological materials at a distance from the catheter tip and minimize contact of the catheter tip with the biological materials.

BRIEF DESCRIPTION OF THE DRAWINGS

FIG. 1 is a side elevational view of an ablation catheter and tip.

FIG. 2 is a fragmentary enlarged section view of the catheter tip having a bulbous configuration.

FIG. 3 is a fragmentary enlarged section view of the catheter tip having a spherical configuration.

FIG. 4 is a fragmentary enlarged section view of a catheter tip having an extended rectangular shape.

FIG. 5 is a fragmentary enlarged section view of a catheter tip having a rectangular shape showing the electrical conduit.

DETAILED DESCRIPTION OF PREFERRED EMBODIMENTS

Figure 11:
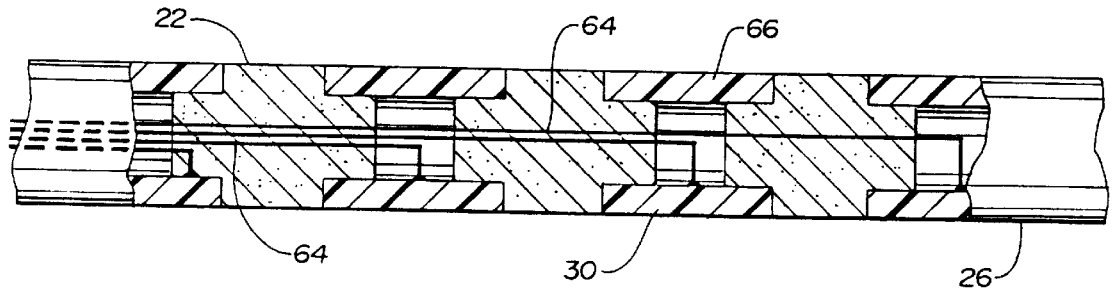
FIG. 11 is a fragmentary enlarged section view of a catheter having ring electrodes which have path means.

The invention relates to a catheter having a fluid perfused or insulated tip. Fluid passes through the tip structure, forming a fluid protective layer around the exterior surface of the tip structure. The fluid which permeates and surrounds the tip structure minimizes the amount of the biological material which comes in contact with the catheter tip structure, as well as cools the tip structure. The cooling fluid prevents a rise in the resistance (impedance) of the tissue to energy transfer from an ablation energy source, and maximizes the potential energy transfer to the tissue in communication with the catheter tip. As a result, a larger lesion size in the tissue is produced.

Referring to FIG. 1, a side elevational view of catheter 20 is shown having catheter body 22, a handle 24, and a tip structure 26. Catheter body 22 may be of varying lengths, the length being determined by the application for catheter 20. Catheter body 22 is preferably made of a flexible, durable material, including thermoplastics such as nylon, in which a braiding is embedded. Preferably, catheter body 22 includes a large central lumen 28, such as a three French (F) lumen in a four F to twelve F, preferably eight F catheter 20. Catheter body 22 may contain a plurality of ring electrodes 30 which surround the exterior surface of catheter body 22 at selected distances from the distal end 32 proximate tip structure 26.

As shown in FIG. 1, handle 24 is positioned on the proximal end 34 of catheter body 22. Handle 24 may contain multiple ports, such as ports 36, 38. Port 36 may be utilized, in this embodiment, for electrical connections between electrophysiological monitoring equipment and electrical potential sites of the tissue. Electrical connection means 40, exiting through port 36, is positioned between and connects tip structure 26 and the electrophysiological monitoring equipment. Port 36 is in communication with central lumen 28 of catheter body 22 and may also be used for the introduction and passage of devices 42 through catheter 20. Port 38, in this embodiment, is connected to a fluid source means and is also in fluid communication with central lumen 28 of catheter 20. Port 38 may be used for the entry of a fluid into catheter 20. Additional ports may be included on handle 24 which are in communication with central lumen 28. Port 36 may, for example, contain electrical connection means 40, and an additional port may contain device 42.

Referring to FIG. 1, tip structure 26 is located at the distal end 32 of catheter body 22. Tip structure 26 may range from four (4) to twelve (12) French catheter tips. Tip structure 26 includes an attachable electrode which can be used for monitoring electrical potentials of the tissue, measuring cardiac signals, and mapping to locate the tissue to be ablated. In addition, the tip structure may include monitoring means for measuring, monitoring, and adjusting the rate of fluid flow through tip 26 relative to biological parameters, such as tip and tissue temperature.

As shown in FIGS. 2–5, the overall shape of tip structure 26 may have a variety of configurations. The various configurations may be machined into the material comprising tip structure 26. Preferably, the shape of tip structure 26 permits catheter 20 to proceed readily through the vein or artery into which catheter 20 may be inserted. The shape of tip structure 26 is determined by the application for which catheter 20 is designed. For example, FIG. 2 is a fragmentary enlarged section view of tip structure 26 having wall portions 27 which extend beyond the diameter D of catheter portions proximal to the tip. For example, a bulbous or dumbbell configuration, as shown in FIG. 2, may be useful in situations requiring access to pathway ablations which lie on top of a valve or other relatively inaccessible site. FIG. 3 illustrates a fragmentary enlarged section view of tip structure 26 which has a spherical or rounded configuration which may be advantageous, for example, in situations involving cardiac pathways underneath a valve. FIG. 4 and FIG. 5 illustrate fragmentary enlarged section views of tip structure 26 which vary in the length of tip structure 26. Tip structure 26 shown in FIG. 4 may be useful in applications which lie along the myocardial wall, and tip structure 26 illustrated in FIG. 5 may be particularly advantageous for uses such as electrophysiological mapping.

Tip structure 26 may comprise a variety of materials. Preferably, the material used for tip structure 26 in the different embodiments may include a plurality of apertures or path means which are either randomly or discreetly formed in or spaced throughout tip structure 26. The diameter of the path means is substantially smaller than the overall diameter of tip structure 26. The diameter dimensions of the path means in the different embodiments discussed below may vary, and may include microporous structures.

As illustrated in FIGS. 2–5, tip structure 26 is preferably made of a sintered metal which contains a plurality of randomly formed through-passages or path means 48 in tip structure 26. Generally, to create the sintered metal for tip structure 26, spherical particles, such as finely pulverized metal powders, are mixed with alloying elements. This blend is subjected to pressure under high temperature conditions in a controlled reducing atmosphere to a temperature near the melting point of the base metal to sinter the blend. During sintering (heating), metallurgical bonds are formed between the particles within the blend at the point of contact. The interstitial spaces between the points of contact are preserved.

Paths means 48 and tip structure 26 comprise interstitial spaces structures which are randomly positioned, are of varying sizes, and are interconnected in a random manner with other interstitial spaces in tip structure 26 to provide fluid communication between central lumen 28 of catheter 20 and the exterior surface 50 of tip structure 26. Path means 48 are generally five to twenty microns in diameter, although this may vary. The metal material utilized for tip structure 26 should conduct heat well, have the ability to monitor electrical potentials from a tissue, and be economical to fabricate, such as stainless steel or platinum.

Figure 6:
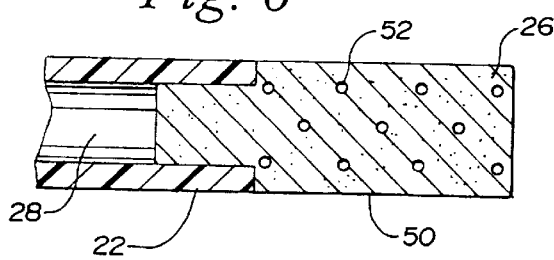
FIG. 6 is a fragmentary enlarged section view of a solid catheter tip having a multiplicity of discreet passages.

Alternatively, as shown in FIG. 6, tip structure 26 may comprise a solid metal material. FIG. 6 is a fragmentary enlarged section view of catheter body 22 connected to tip structure 26. Tip structure 26 in this embodiment comprises a solid metal, such as stainless steel or platinum, having a multiplicity of specifically formed apertures or path means 52 within tip structure 26 which provide fluid communication between central lumen 28 of catheter 20 and the exterior surface 50 of tip structure 26 for the passage of a fluid. Position of path means 52 are designed to provide a continuous layer of fluid over the exterior surface 50 of tip structure 26. Preferably, the apertures of path means 52 have a diameter less than five hundred microns, although this may vary. The metal material utilized for tip structure 26 shown in FIG. 6 should conduct heat, as well as have the ability to monitor electrical potentials from a tissue.

Figure 7:
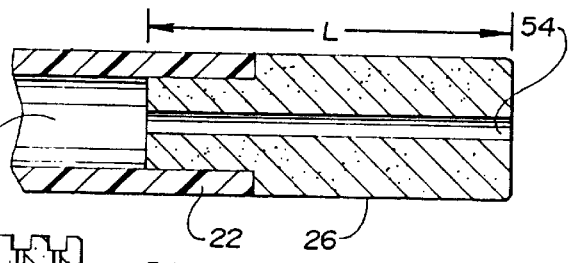
FIG. 7 is a fragmentary enlarged section view of a solid catheter tip having a passage extending the length of the catheter tip.

FIG. 7 is a fragmentary enlarged section view illustrating catheter body 22 attached to tip structure 26. Tip structure 26, in this embodiment, is preferably made of a solid metal material which conducts heat well, and has the ability to monitor and measure electrical potentials of a tissue, such as stainless steel or platinum. Alternatively, tip structure 26 may comprise a dense ceramic material. As shown in FIG. 7, a single orifice, channel or through path means 54 is formed through the length L of tip structure 26. Path means 54 is in fluid communication with central lumen 28 of catheter 20. Preferably, the aperture of path means 54 has a diameter less than five hundred microns, although this may vary.

Figure 9:
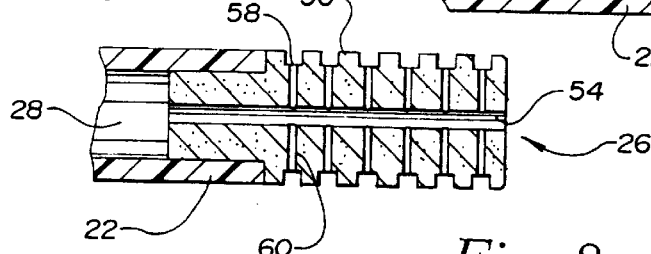
FIG. 9 is a cross section view of the catheter tip showing a multiplicity of radially directed channels encircling the catheter tip.
Figure 8:
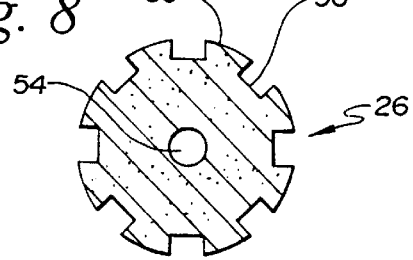
FIG. 8 is a cross section view of the catheter tip showing axial channels extending the length of the catheter tip.

FIGS. 8 and 9 illustrate alternative cross section embodiments of tip structure 26 shown in FIG. 7. FIG. 8 illustrates tip structure 26 having a plurality of grooves or directional channels 56 which extend in an axial direction along the length L of tip structure 26. Interconnecting channels may extend radially between channels 56 to aid in the fluid distribution over tip structure 26. FIG. 9 illustrates a plurality of annular grooves or directional channels 58 which encircle tip structure 26 in a radial manner. As shown in FIG. 9, channels 60 extend between path means 54 and channels 58 to direct the fluid flow through central lumen 28 and path means 54 to the exterior surface 50 of tip structure 26. In these embodiments, channels 56, 58 are designed to communicate with path means 54 to provide a continuous, evenly distributed fluid protective layer over substantially the entire exterior surface 50 of metallic tip structure 26.

Figure 10:
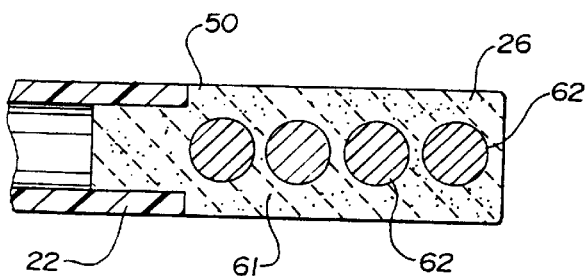
FIG. 10 is a fragmentary enlarged section view of a catheter tip made of a ceramic insulating material having monitoring members.

Referring to FIG. 10, an alternative embodiment of tip structure 26 is shown. FIG. 10 is a fragmentary enlarged section view of catheter body 22 attached to tip structure 26. Tip structure 26, in this embodiment, preferably comprises a ceramic insulating material which includes randomly formed path means 61. Path means 61 are generally five to twenty microns in diameter, although this may vary. Path means 61 are in fluid communication with central lumen 28 of catheter 20. In addition, tip 26 includes at least one monitoring member 62 positioned throughout tip structure 26. Member(s) 62 may be of varying shapes and dimensions. Preferably, members 62 are made of a conductive material suitable for monitoring electrical activity and for application of electrical energy to a biological tissue, such as stainless steel or platinum. Tip structure 26, in this embodiment, may contain axial or radial directional channels on exterior surface 50 of tip structure 26.

As shown in FIGS. 1 and 11, ring electrodes 30 may be attached to catheter body 22. Ring electrodes 30 are connected to the monitoring equipment by electrical connection means 64 through port 36 in handle 24. Electrical connection means 64 are attached to ring electrodes 30, by, for example, soldering or other suitable mechanical means. Ring electrodes 30 may be made of a material which has path means similar to path means 48, 52, 60 as described above with reference to tip structure 26 in FIGS. 2–5 and 10, and is preferably a sintered metal material. A plurality of ring electrodes 30 may be positioned at distal end 32 of catheter 20. Ring electrodes 30 may be used for electrophysiological monitoring and mapping, as well as for ablation. Fluid passes from central lumen 28 through path means 48, 52, 61 in ring electrodes 30 to form a fluid protective layer around the exterior surface 66 of ring electrodes 30.

Figure 14:
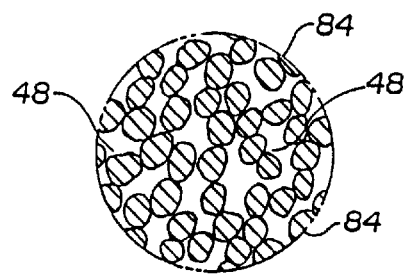
FIG. 14 is an enlarged fragmentary sectional view of a portion of the catheter tip and ring electrodes shown in FIGS. 2–5, 10, and 11.

FIG. 14 illustrates an enlarged fragmentary section view of a portion of catheter tip structure 26 and/or ring electrodes 30 shown in FIGS. 2–5, 10, and 11. Substantially spherical particles 84, preferably biologically compatible metal particles, are positioned and arranged so as to form and create numerous interconnected, omnidirectional, tortuous path means 48, 52, and 61 (only 48 shown) through tip structure 26. Fluid flows through these tortuous path means 48, 52, 61 in the varied tip structure configurations to the exterior surface 50 of tip structure 26 or exterior surface 66 of ring electrodes 30 to uniformly and evenly distribute the fluid around tip structure 26. Substantially all path means 48, 52, 61 at surface 50 of tip structure 26 or surface 66 of ring electrodes 30 is connected through the tortuous paths to central lumen 28.

The fluid introduced through port 38, or an additional port, of catheter 20 is preferably a biologically compatible fluid, and may be in a gaseous or liquid state. For example, the fluid may comprise carbon dioxide, nitrogen, helium, water, and/or saline. Fluid enters through, for example, port 38 and is passed though central lumen 28 of catheter body 22. The fluid perfuses tip structure 26 and/or ring electrodes 30 through the path means in tip structure 26 and/or ring electrodes 30, and creates a fluid protective layer surrounding exterior surface 50 of tip structure 26 or exterior surface 66 of electrodes 30, thereby minimizing contact of tip structure 26 or electrodes 30 with biological material, such as blood. The rate of fluid flow through central lumen 28 of catheter 20 may vary and range from 0.1 ml/min. to 40 ml/min. Fluid flow through catheter 20 may be adjusted by a fluid infusion pump, if the fluid is liquid, or by pressure, if the fluid is a gas. The fluid flow is regulated by the infusion pump for the liquid fluid, or by a needle valve if a gas, so as to maintain an optimal disbursing flow over tip structure 26 and/or ring electrodes 30 and maintain a desired tip temperature. Preferably, the protective layer of fluid covers all or substantially all of the surface area of tip structure 26 and is between about 0.001 mm and one (1) mm, and more preferably, about 0.01 mm. in thickness, although this may vary depending on the application, and may vary in thickness during a given procedure.

Temperature sensing means 47 may be incorporated into tip structure 26 for sensing and measuring the temperature of tip structure 26 and for sensing and measuring the temperature of the biological tissue in contact with tip structure 26 as shown in FIG. 3 and FIG. 4. Temperature sensing means 47 may be incorporated in any of the tip structure embodiments shown in FIGS. 2–10. The temperature sensing means generally comprises at least one temperature sensor, such as a thermocouple or thermistor. In addition, temperature sensing means 47 may be utilized as a feedback system to adjust the flow rate of the biologically compatible fluid to maintain the temperature of the tip structure at a particular temperature within a designated range of temperatures, such as 40° C. to 95° C. Also, temperature sensing means 47 may be used as a feedback system to adjust the flow rate of the biologically compatible fluid so as to maintain the temperature of the biological tissue in contact with tip structure 26 at a particular temperature within a designated range of temperatures, such as 40° C. to 95° C. The temperature of the tissue or tip structure 26 is controlled by the temperature of the fluid, the distribution of the fluid relative to internal and external surfaces to the tip structure, the energy applied to the catheter, and the fluid flow rate.

Catheter 20 may include ablation means within tip structure 26. Preferably, the ablation means may be a wire connected to an RF energy source, although other types of electrical energy may be utilized, including microwave, ultrasound, and direct current. Alternatively, the ablation means may include optical fibers for delivery of laser energy. The ablation means may be connected to an energy source through port 36, or an additional port.

As shown in FIG. 1, device 42 may be passed through central lumen 28 of catheter 20. Device 42 may include, for example, a guidewire for ease of entry of catheter 20 into the heart or vascular system; a diagnostic device, such as an optical pressure sensor; a suction catheter for biopsy of biological material near the distal tip; an endoscope for direct viewing of the biological material in the vicinity of the distal tip of the catheter; or other devices.

Figure 12:
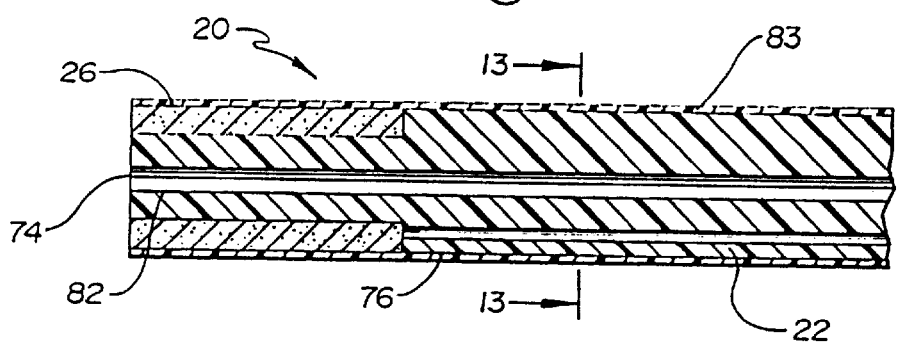
FIG. 12 is a fragmentary enlarged section view of an alternative embodiment of a catheter having a large central lumen and a smaller lumen.
Figure 13:
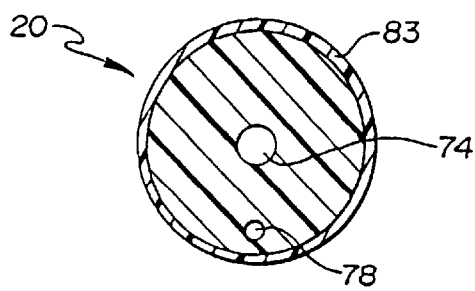
FIG. 13 is a cross section view taken along line 13—13 of FIG. 12.

FIG. 12 and FIG. 13 illustrate another embodiment of catheter 20. A central lumen 74 extends the length of catheter 20. Distal end 76 of catheter 20 may include a smaller diameter lumen 78 relative to lumen 74 positioned substantially parallel and adjacent to central lumen 74. Lumen 74 permits the introduction of a device, such as described above regarding device 42, through the center of catheter 20, as well as the passage of the fluid. Lumen 78 may be connected to port 38, and may also be used to direct the fluid to tip structure 26, such that the fluid passes through path means 48, 52, 54, 61 in tip structure 26, as discussed above in relation to FIGS. 2–10. Non-permeable layer 82, such as a plastic liner layer, may be positioned between lumen 74 and lumen 78 to ensure that the fluid in lumen 78 is directed through passages or path means 48, 52, 54, 61 in tip structure 26 to the exterior surface 50 of tip structure 26. Ring electrodes may also be used in this embodiment to direct fluid to the exterior surface of tip structure 26 and catheter 20.

In operation, catheter body 22 of catheter 20 is percutaneously inserted into the body. Catheter 20 may be articulable for ease of insertion into the body. Catheter body 22 is positioned in the heart or vascular system. Tip structure 26, as an electrode, may be utilized to measure electrical potentials of the tissue and provide information regarding cardiac signal measurement. Electrical connection means 40 extends from tip structure 26, through port 36, and is connected to monitoring equipment. Tip structure 26 may be utilized to map, monitor, and measure the cardiac signals and electrical potentials of the tissue, and locate arrthymogenic sites.

A biologically compatible fluid is introduced through port 38. The fluid passes through a central lumen of catheter body 22 and is directed to tip structure 26. The fluid passes through tip structure 26 and/or ring electrodes 30 through path means 48, 52, 54, 61, in a manner determined by the embodiment of tip structure 26 used. The fluid perfuses tip structure 26 and forms a fluid protective layer around exterior surface 50 of tip structure 26 and/or exterior surface 66 of ring electrodes 30. The fluid layer formed around catheter tip structure 26 and/or ring electrodes 30 maintains biological materials, such as blood, at a distance from catheter tip structure 26, thereby minimizing contact of catheter tip structure 26 with the biological material, as well as cooling tip structure 26. Since there is a consistent, controlled buffer layer between the biological material and catheter tip structure 26, the coagulation of biological fluids on catheter tip structure 26 is reduced and the impedance or resistance to energy transfer of the tissue in communication with catheter tip structure 26 is regulated and minimized.

Once the site has been located by the monitoring of the electrophysiological signals of the tissue, the ablative energy is activated. As a result of the fluid protective layer, the transfer of electrical energy to the tissue is enhanced. Increased destruction of cardiac tissue also results from tip structure cooling since larger and deeper lesions in the cardiac tissue are achieved than have been previously possible.

The flow rate of the fluid over exterior surface 50 of tip structure 26 or exterior surface 66 of ring electrodes 30 may be accomplished in a controlled manner so that a thin fluid film is formed around exterior surface 50, 66 of tip structure 26 and ring electrodes 30. The maintenance of a controlled, stable, uniform fluid film along substantially the entire exterior surface of tip 26 and ring electrodes 30 may be accomplished by using the various embodiments of tip structure 26 described above having a multiplicity of passages or path means 48, 52, 54, 61. Path means 48, 52, 54, 61 permits an even, consistent distribution of minute quantities of a biologically compatible fluid over substantially the entire tip exterior surface 50 or ring electrodes exterior surface 66. The fluid can be pumped through tip structure 26, or heat generated by the electrical or ablation process can be used to expand the fluid and create a movement of fluid to the exterior surface 50, 66 of tip structure 26 or ring electrodes 30. This movement of fluid provides a buffer or protective insulating layer between the exterior surface of tip structure 26 and the biological material, such as blood, thereby reducing the coagulation of biological materials on tip structure 26. In addition, the movement of fluid over and around tip structure 26 may be aided by passages or channels 56, 58 on exterior surface 50 of tip structure 26. Cooling of tip structure 26 increases the lesion size produced by the ablation means since the point of maximum tissue temperature is likely moved away from tip structure 26, which allows for an altered tissue heat profile, as further described below.

A control system may be included for controlling and regulating the electrical potentials and temperatures in a manner that allows for determination of the ablation effects in the tissue. It is possible to control the distribution of tissue heating by controlling the temperature of tip structure 26 and the radiofrequency voltage, or other energy used, applied between tip structure 26 and a reference electrode on the surface of the body. The voltage may be set to achieve a desired electrical field strength, and the temperature of tip structure 26 may be set to provide a desired temperature distribution of the tissue. The temperature distribution will then determine the size of the lesion, i.e., the denatured protein dimensions in the myocardium.

The fluid flow rate can be regulated relative to biological parameters, such as tissue temperature, by the temperature sensing means. For instance, if the temperature of the tissue increases, the fluid flow rate can be increased by the regulation of the fluid infusion pump or gas needle valve. If the tissue temperature adjacent tip structure 26 is not high enough, the fluid flow rate can be decreased. This permits power to be set independently of temperature. It is significant to note that it is normally not necessary to remove the introduced fluid from the body.

Another advantage of the fluid layer buffering the surface area of tip structure 26 and/or ring electrodes 30 is that the fluid layer also cools the tissue adjacent tip structure 26 during ablation. In addition, the fluid aids in maintaining the cardiac tissue adjacent tip structure 26 in a cooler and potentially more conductive state, which permits more electricity or ablative energy to enter the tissue. As a result, larger lesions are produced because a larger voltage can be applied, producing a larger electric field without producing excessive temperatures and coagulum formation at the tip/tissue interface. In addition, the greater the pressure of the fluid, the more biological products are kept from the field of influence of, or area surrounding, tip structure 26.

It is also possible to generate reversible affects of ablation by use of a cooling fluid down the central lumen 28 of catheter 20 and tip structure 26, or by use of a low temperature controlled or elevational heating. An area in the heart tissue is quenched with a cold or icy fluid to produce a tissue temperature of 0° C. to 30° C., or heated with electrical energy with closed loop temperature controls as described above to produce tissue temperatures ranging from 40° C. to 48° C. Those cool and warm temperatures slow the conduction of signals and temporarily and reversibly eliminate the conduction pathways. This technique may be advantageously used to see the affect on the tissue before the tissue is permanently affected. The heart tissue gradually heats or cools back to normal. This technique is also advantageous since no catheter exchange would be required.

As has been described, one of the major problems with the application of radiofrequency ablation energy in a cardiac environment is the coagulation of blood onto the catheter tip, creating a high impedance, that is, a high resistance to passage of electrical energy into the tissue. As impedance increases, more energy is passed through the portion of the tip without coagulation, creating even higher local temperatures and further increasing coagulum formation and impedance. Eventually, the catheter must be removed from the vascular system, the catheter tip cleaned and the catheter repositioned within the vascular system at the desired location. The repositioning process is extremely disadvantageous, because it is time consuming and because the reduced electrical activity in the regions that have been previously ablated may make it difficult to return the catheter to the previous location. Therefore, it is well-recognized in the art that eliminating impedance rise is a very desirable objective.

In the ablation catheter field, the term "impedance rise" generally means an increase in impedance that renders delivery of ablative energy impossible, that is, an impedance rise up to 200 ohms or more. Typically, coagulation of biological material onto the catheter tip causes the increase in impedance. Catheters according to embodiments of the invention, however, preclude ablation-inhibiting impedance rise, as has previously been described.

In an attempt to prevent impedance rise in ablation catheters, Nakagawa et al. tested a 7 F deflectable catheter with a lumen and a 5 millimeter tip electrode containing 6 irrigation holes. (Nakagawa, H., et al., *Effective Delivery of Radiofrequency Energy through the Coronary Sinus without Impedance Rise using a Saline Irrigated Electrode*, Abstract, JACC, February 1995.) With saline irrigation at 60 ml/min during ablation, RF applications were delivered at 45±5 watts, a standard maximum power deliverable by currently used ablation catheters. Despite the application of standard wattage, and despite the relatively high 60 ml/min fluid flow rate, impedance rise, that is, ablation-inhibiting impedance rise as described above, was detected in 3 out of 18 trials.

Nibley et al. (Nibley, C., et al., *Predictors of Abrupt Impedance Rise During Chilled-Tip Radiofrequency catheter Ablation*, Abstract, JACC, February, 1995) and Wharton et al. (Wharton, J. M., et al., *Establishment of a Dose-Response Relationship for High Power Chilled-Tip radiofrequency Current Ablation in Sheep*, Abstract, JACC, February, 1995) also have recognized impedance rise as a significant problem. In experiments using internally cooled catheters, Nibley et al. confirmed that frequency of impedance rise increases with increased power. Even at applied powers of only 40 watts, impedance rise was detected in 8.3% of Nibley et al.'s trials. At 70 watts, over 70% of trials suffered impedance rise. Wharton et al. noted that power application beyond only 50 watts was progressively limited by early impedance rise and was associated with diminished lesion volume.

It also is desirable during ablation procedures to introduce as little fluid as possible into the cardiovascular system. With introduction of more than one liter of fluid, even patients with healthy cardiovascular systems generally require treatment, such as diuretic therapy, to counteract the introduced fluid. For diseased hearts, countervailing medical treatment should begin with introduction of as little as 0.5 liters of fluid. As discussed previously, irrigation during ablation using the Nakagawa et al. catheter occurred at a rate of 60 ml/min. Consequently, for a diseased heart, countervailing medical treatment would have to occur after less than 9 minutes of ablation, that is, 9 minutes of irrigation at that rate. For a healthier patient, such treatment would have to begin after less than 17 minutes of ablation. As most ablation procedures typically require 15–30 minutes of active ablation, diuretic or other such therapy must be instituted during the procedure, adding to the physiological stress on the patient.

Embodiments of the above-described catheter overcome the previously described disadvantages. As will be described with reference to animal studies that have been conducted, discussed below, embodiments of the above-described catheter did not suffer any impedance rise, that is, ablation-inhibiting impedance rise, even for powers up to 100 watts. Additionally, tested embodiments of the catheter permitted the introduction of significantly less fluid into the patient. The absence of impedance rise and reduction in fluid allowed substantially larger lesions to be formed than are possible when impedance rise necessitates removing the catheter for cleaning.

The first of the two studies is described in Appendix A, which is incorporated herein by reference. The study was conducted in Oklahoma City on Dec. 21, 1994. For catheters that were properly placed and properly operating, no impedance rises were detected during the ablation trials, even with power levels as high as 90 watts and with fluid flow rates of 15 ml/min or less. For example, as shown in the raw data at the end of Appendix A, dog no. 2 received lesion LV3 by administration of 2160 Joules over 24 seconds, yielding an average applied power of 90 watts, with a fluid flow rate of 15 ml/min. Despite the magnitude of applied power—twice that applied in the above-described Nakagawa et al. study—and despite the minimal fluid flow one quarter that of the Nakagawa et al. study—no impedance rise was detected. Similarly, for lesion LV2, dog no. 2 received 5400 Joules over 60 seconds, yielding an average applied power of 90 watts, with a fluid flow rate of 15 ml/min. Again, no impedance rise was detected. In fact, no impedance rise was detected during any proper lesion application reflected by the raw data.

The second study of the two studies is described in Appendix B, which is incorporated herein by reference. The second study was conducted in Boston on Feb. 14, 1995. In the Boston study, no impedance rises were detected during ablation procedures performed by successfully placed and properly operating catheters, even with power levels as high as 55 watts and with fluid flow rates of 7.5 ml/min or less. For example, as shown in the raw data at the end of Appendix E, during study no. 4, sheep no. 3 received 55 watts for 60 seconds, equating to a delivered energy of 3300 Joules for lesions nos. 1–2, 5, 7–8, and 11–13. Despite the high power applied and the low fluid flow rate of 7.5 ml/min, no impedance rise of an ablation-inhibiting nature was detected for any of these lesions. For that matter, no impedance rises were detected for any of the lesions applied to any of the six animal subjects used during this study.

The total absence of impedance rise in catheters according to embodiments of the invention, as reflected in the Oklahoma City and Boston studies, allows higher wattages to be applied over longer periods and with lower fluid flow rates. This is extremely advantageous, because the catheter need not be removed for cleaning and then reinserted. Further, therapeutic measures to counter the introduction of excess fluid to the patient are avoided.

Because high powers can be applied for long periods, and because a relatively low amount of fluid is introduced to the patient, embodiments of the catheter according to the invention can be used to create significantly larger and deeper lesions during a single ablation procedure than are achievable with current ablation catheters that must be removed for cleaning due to impedance rise. In the Oklahoma City study, for example, for dog no. 2, lesions RV1 and LV3 were 15×12×10 and 15×13×9 mm, respectively. In the Boston study, for sheep no. 3, lesions 12 and 13 were 20×12×4 and 16×6×3 mm, respectively. The lesions produced during the Nakagawa et al. experiments, on the other hand, were significantly smaller. For approximately 45 watts, for example, lesion diameter was only approximately 7.6 mm. Additionally, large lesion sizes are achievable with embodiments according to the invention relative to solid and drilled catheters, as is described in Bergau, D., et al., *Porous Metal Tipped Catheter Produces Larger Radiofrequency Lesions Through Tip Cooling,* Abstract, AHA, November, 1993.

The absence of impedance rise and the low fluid flow rates associated with the catheter embodiments according to the invention, combined with the capability to create larger lesions, represent significant advances and advantages over prior art catheters.

For a 4 mm (0.160 in) porous tip according to an embodiment of the invention with a diameter of 3 French (0.104 in), area=$(\pi)(0.104)(0.160)$=(0.523 in$^2$)((25.4 m/in)$^2$=33.73 mm$^2$. For preferred, high-wattage (e.g. 100 W) flow rates of 5, 10, and 15 ml/min, specific flow=0.148, 0.296, and 0.444 ml/mm$^2$/min, respectively. Thus, a tip according to the invention causes more efficient cooling, minimizing the amount of fluid (coolant) flow required per surface area for the delivered energy.

What is claimed is:

1. An ablation catheter that reduces coagulation of biological materials on a tip of the catheter by precluding ablation-inhibiting impedance rise of biological tissue adjacent the tip, the ablation catheter comprising:

a tip positioned at a distal end of the catheter to monitor electrical potentials and to apply ablation energy to a biological tissue, the tip having an exterior surface;

a fluid source positioned to supply a fluid flow through the catheter to the tip; and structure defining a plurality of passages comprising interconnected interstitial spaces within the tip to direct fluid flow through the tip toward the exterior surface of the tip and to preclude ablation-inhibiting impedance rise of biological tissue adjacent the tip.

2. The ablation catheter of claim 1, further comprising ablation means at the tip for applying the ablation energy to the biological tissue.

3. The ablation catheter of claim 1, further comprising monitoring means at the tip for measuring electrical potentials within the biological tissue.

4. The ablation catheter of claim 1, wherein the structure defining the plurality of passages provides a fluid protective layer to minimize contact of the tip with biological materials.

5. The ablation catheter of claim 1, wherein the tip applies at least 100 W of ablation energy to the tissue while the structure defining a plurality of passages directs fluid flow toward the exterior surface at a rate of no more than 15 ml/min.

6. A catheter tip for signal measurement and monitoring, the catheter tip comprising:

an exterior surface;

means for providing fluid communication and commensurate flow of fluid from inside the tip to portions of the exterior surface of the tip through a plurality of randomly formed passages that direct the fluid flow from inside the tip over the exterior surface of tip; and monitoring means within the tip for measurement of electrical potentials in a biological tissue.

7. The catheter tip of claim 6, wherein the means for providing fluid communication and flow provides a fluid protective layer at the exterior surface of the tip to minimize contact of the tip with biological materials.

8. The catheter tip of claim 7, wherein the fluid protective layer is a continuous fluid protective layer surrounding the tip.

9. The catheter tip of claim 8, wherein the fluid protective layer covers the entire exterior surface of the tip.

10. The catheter tip of claim 6, wherein the means for providing fluid communication and flow cools the tip to cool biological tissue adjacent the tip.

11. The catheter tip of claim 6, wherein the means for providing fluid communication and flow comprises structure defining a plurality of randomly disposed interstitial spaces.

12. An ablation catheter for delivering ablation energy to biological tissue, the ablation catheter comprising:

a tip disposed at a distal end of the ablation catheter to deliver at least 70 W of ablation energy to the tissue, the tip having an exterior;

a fluid source disposed at a proximal end of the ablation catheter;

an internal lumen extending through the catheter to provide fluid communication between the fluid source and the tip; and path structure within the tip to direct fluid flow from the internal lumen toward the exterior of the tip at a flow rate of no more than 10 ml/min for 70 W of ablation energy, the catheter precluding ablation-inhibiting impedance rise.

13. The ablation catheter of claim 12, wherein the path structure directs fluid flow evenly over the exterior of the tip.

14. The ablation catheter of claim 13, wherein the path structure directs the fluid flow to form a protective layer over the exterior of the tip.

15. The ablation catheter of claim 14, wherein the protective fluid layer is a continuous layer.

16. The ablation catheter of claim 14, wherein the protective fluid layer surrounds the tip.

17. The ablation catheter of claim 12, wherein fluid flow through the path structure cools the tip.

18. The ablation structure of claim 12, wherein the path structure provides a specific flow of at least $0.29$ ml/mm$^2$/min. for a 10 ml/min. flow rate and at least 70 W of delivered ablation energy.

19. An ablation catheter for application of energy to biological tissue, the ablation catheter comprising:

a proximal end, a distal end and at least one lumen;

a tip at the distal end of the catheter, the tip including at least one electrode through which ablative energy is applied to the biological tissue, the electrode having an external surface;

a plurality of fluid paths disposed through the electrode, the fluid paths being generally between 5 and 20 microns in diameter and being constructed to direct fluid from the lumen through the electrode to the external surface of the electrode to form a protective layer of fluid around the electrode; and a fluid source for directing fluid through the lumen and the plurality of fluid paths to the external surface of the electrode.

20. The ablation catheter of claim 19, wherein the electrode comprises a ring electrode.

21. The catheter of claim 19, wherein the electrode comprises a microporous structure.

* * * * *